United States Patent
Beckman

(10) Patent No.: US 9,189,668 B2
(45) Date of Patent: Nov. 17, 2015

(54) OBJECT CONDITION ANALYSIS AND CONTROL TECHNIQUES

(71) Applicant: GROUP MEE, LLC, Brooklyn, NY (US)

(72) Inventor: Christopher V. Beckman, San Diego, CA (US)

(73) Assignee: Mymee, LLC, Brooklyn, NY (US)

(*) Notice: Subject to any disclaimer, the term of this patent is extended or adjusted under 35 U.S.C. 154(b) by 292 days.

(21) Appl. No.: 13/830,280

(22) Filed: Mar. 14, 2013

(65) Prior Publication Data
US 2014/0266630 A1     Sep. 18, 2014

(51) Int. Cl.
| | | |
|---|---|---|
| *H04Q 5/22* | (2006.01) | |
| *H04Q 5/20* | (2006.01) | |
| *G06K 7/10* | (2006.01) | |
| *G06Q 10/08* | (2012.01) | |
| *G06Q 50/22* | (2012.01) | |

(52) U.S. Cl.
CPC ............ *G06K 7/10366* (2013.01); *G06Q 10/08* (2013.01); *G06Q 50/22* (2013.01)

(58) Field of Classification Search
None
See application file for complete search history.

(56) References Cited

U.S. PATENT DOCUMENTS

| | | | | |
|---|---|---|---|---|
| 5,565,858 | A  * | 10/1996 | Guthrie | 340/10.33 |
| 7,581,108 | B1 * | 8/2009 | Bohm et al. | 713/178 |
| 7,782,189 | B2 * | 8/2010 | Spoonhower et al. | 340/539.12 |
| 2012/0024889 | A1 * | 2/2012 | Robertson et al. | 222/23 |
| 2012/0101874 | A1 * | 4/2012 | Ben-Haim et al. | 705/14.1 |
| 2013/0048737 | A1 * | 2/2013 | Baym et al. | 235/492 |

* cited by examiner

*Primary Examiner* — Brian Zimmerman
*Assistant Examiner* — John Bamert

(57) ABSTRACT

New consumption and inventory recording, tracking, analysis and control techniques are provided. In some aspects of the invention, multiple master tags and signal control elements manage the communication of unique signals indicating and managing inventory status and consumption activity. A master tag may bridge communication from a computer hardware and software control system to smaller, more shielded inventory tags, to assess unique identifying information and control actuation of various functions. In other aspects, drugs and other agents may be variably released and/or applied by a new form of actuable, consumable tag with multiple signal elements.
A computer display with specialized software may comprise part of the control system, and may reflect, provide, and/or receive modified data signals to and from such tags and signal elements.
In other aspects of the invention, an administrative user may use a GUI to access information concerning, and control, consumption by a consumer user.

20 Claims, 9 Drawing Sheets

OBJECT CONDITION ANALYSIS AND CONTROL TECHNIQUES

COPYRIGHT AND TRADEMARK NOTICE

© Copyright 2013 Christopher V. Beckman. A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. Unless otherwise stated, all trademarks disclosed in this patent document and other distinctive names, emblems, and designs associated with product or service descriptions, are subject to trademark rights. Specific notices also accompany the drawings incorporated in this application; the material subject to this notice, however, is not limited to those drawings.

FIELD OF THE INVENTION

The present invention relates to object recognition and motion tracking sensors and control systems.

BACKGROUND

Human beings have implemented purposeful diets, exercise, medical regimens and other activities and routines ("personal activities") for centuries, in an effort to restore, maintain or enhance personal health and physical performance.

In recent years, research has confirmed that the degree, frequency and type of personal activities can have profound affects on a person's overall morbidity and mortality. For example, it has long been understood that sedentary lifestyles are strongly associated with adverse health conditions and the risk of premature death. Flowing from this, millions of Americans now attempt to follow the advice of health professionals that they should make an effort to exercise frequently. When provided, a physician's specific advice may vary widely, but guidelines from the Centers for Disease Control recommend: (1) a minimum of 150 minutes of moderate-intensity or 75 minutes of vigorous-intensity aerobic activity, and (2) muscle-strengthening activities on 2 or more days a week that work all major muscle groups, among other possible regimen combinations for health benefits.

Strikingly, a majority of patients are still not advised to exercise at all by their physician, even in the face of recent studies establishing that a majority of adults in the United States are overweight or obese.

In recent years, the sufficiency and soundness of general advice on exercise from health authorities has been called into question by empirical research. Several studies now demonstrate that even a high level of regular, moderate-to-vigorous exercise may be insufficient to offset the destructive effects of time spent sitting. Findings like these are extremely important today, because more and more workers in the United States spend most of their time sitting at work—specifically, while working at personal computer terminals. Many of these workers continue to labor under the delusion that, if they spend a half an hour at the gym on a lunch break or after work, they can offset the effects of a sedentary work routine. In fact, some studies may even support the disturbing conclusion that a person may actually be less active, overall, on days that they make an effort to exercise vigorously, offsetting the benefits.

Adherence to medical regimens and compliance with consumption-related instructions from medical and fitness personnel also presents long-standing, serious challenges for millions. In recent years, a plethora of medical compliance tools (such as reminder systems and calendared medicine containers) have flourished, but the issue of compliance with such regimens continues.

It should be understood that the disclosures in this application related to the background of the invention, in, but not limited to this section titled "Background," do not necessarily set forth prior art or other known aspects exclusively, and may instead include art that was invented concurrently or after the present invention and conception, and details of the inventor's own discoveries and work and work results.

SUMMARY OF THE INVENTION

New object inventory, recording, tracking, analysis and control techniques are provided. In some aspects of the invention, multiple master tags and signal control elements (such as inventory tags) manage the communication of unique signals indicating inventory status and consumption activity, and managing that consumption. A master tag may bridge communication from a computer hardware and software control system to smaller, more shielded inventory tags, to assess unique identifying information and control actuation of various functions. In other aspects, drugs and other agents may be variably released and/or applied by a new form of actuable, consumable tag with multiple signal elements, and other selectable actuation techniques may be carried out.

A computer display with specialized software may comprise part of the control system (which may include a computer), and may both receive, provide, reflect and/or receive reflected (or modified and reflected) data signals to and from such tags and signal elements.

In other aspects of the invention, an administrative user may use a GUI interface with the control system (which may be on a computer system, or may be in communication with a PDA) to access information concerning, and control, consumption by a consumer user.

In still other aspects of the invention, activity pattern recognition is also greatly improved by a new type of tag- and thermal data-assisted object recognition as well as system-wide and location-specific information sharing. In addition, the system may simplify its analysis by focusing data gathering into a variably-defined personal activity space. With respect to the tag(s), the detectable identity of tags may be assigned by an aspect of the system and/or a user, after which their identity, range and/or more specific location in space relative to a user may be assessed. After that time, a smartphone, PDA or other user-defining system aspect with a near-field, tag-pinging or other communication sub-system identifies relevant tag(s), their location relative to the user, and contributes that information in aid of defining the user's activity patterns. Other activity pattern data contributed to the system for activity and activity pattern analysis and recordation are positional, movement, orientation and acceleration data, which may be contributed by conventional GPS, accelerometer and other methods. Activity mapping (including algorithms applied by the system for the definition of tagged areas and sub-areas by many different users) may aid the system in identifying and ascribing relevant environmental and activity qualities to the tags.

In some aspects of the invention, identifying beacons are used, for example from a local base station defining an environmental area, in addition to or in place of tags, to aid in area, article and other environmentally-relevant activity definition.

The system may also benefit from implementing local object recognition, benefiting from a new form of thermal differential analysis, to aid in identifying consumption and other activity. For example, the system may obtain information relevant to consuming foodstuffs, including the potential food type, size and caloric properties, among other consumption and other activity-relevant data.

Further aspects of the invention and specific embodiment will be set forth below, with reference to the drawings.

CANONS OF CONSTRUCTION AND DEFINITIONS

The following terms shall have the following meanings, significance and senses, in addition to their ordinary and specific meanings, significances and senses in general usage and within the technological field(s) in which they are used. "GUI," in addition to its ordinary meaning and special meaning in the arts to which it relates and that may be relevant to this application, means any device, object, method or technique comprising controls assisting or enabling a user to carry out or affect the performance, actuation, parameters, or other aspects of the invention, or any part thereof. A GUI comprises, but is not limited to, virtual controls, or a set thereof, represented by computer hardware and software (for example, actuable visual representations of tools by a computer system on a computer screen).

Where any term is set forth in a sentence, clause or statement ("statement"), each possible meaning, significance and/or sense of any term used in this application should be read as if separately, conjunctively and/or alternatively set forth in additional statements, as necessary to exhaust the possible meanings of each such term and each such statement.

It should also be understood that, for convenience and readability, this application may set forth particular pronouns and other linguistic qualifiers of various specific gender and number, but, where this occurs, all other logically possible gender and number alternatives should also be read in as both conjunctive and alternative statements, as if equally, separately set forth therein.

DETAILED DESCRIPTION OF THE INVENTION

Figure 1:
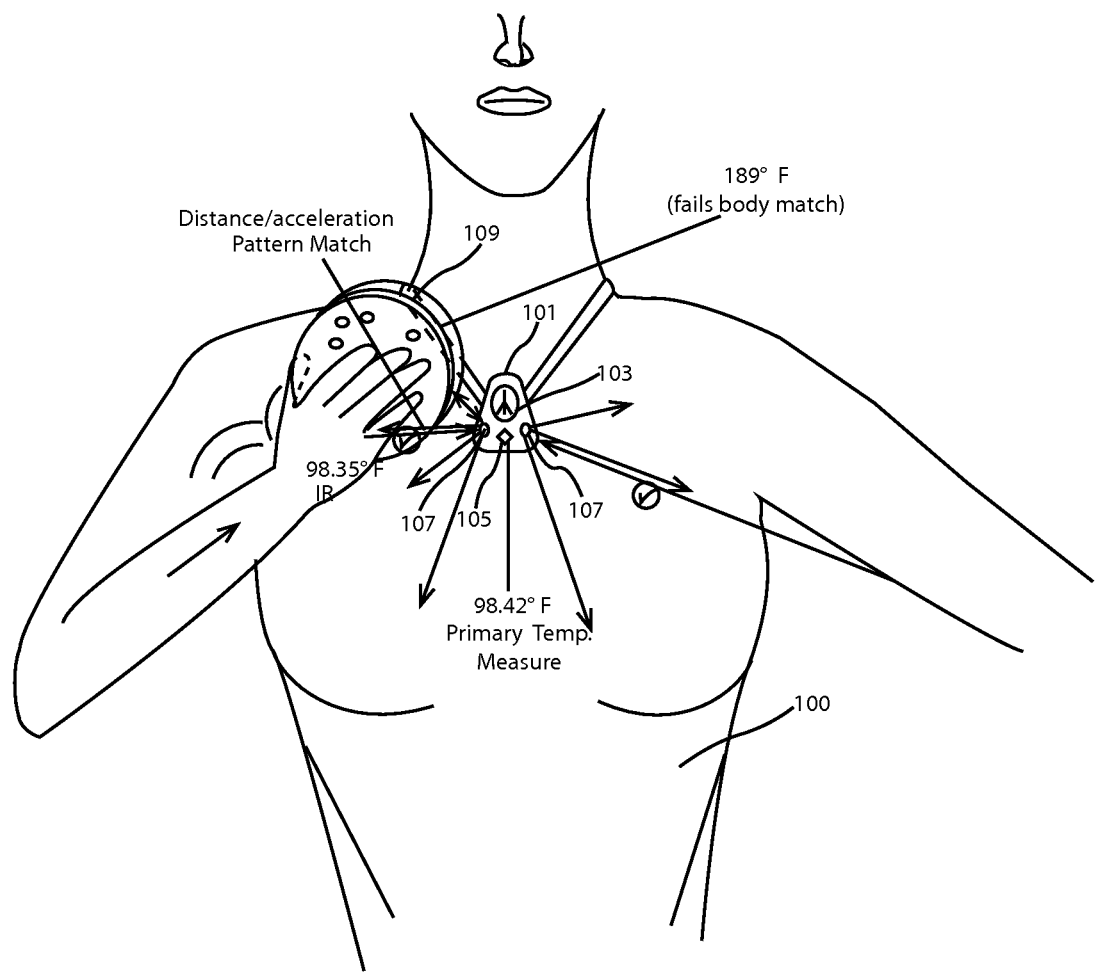
FIG. 1 is a front perspective view of a user whose activity is being tracked by an exemplary system implementing aspects of the invention.

FIG. 1 is a front perspective view of a user 100 whose activity is being tracked by an exemplary system implementing aspects of the invention. A radiation transceiver device 101 is an aspect comprised in that system, and includes a series of additional, sub-aspects. Each aspect may be variably or permanently networked or otherwise connected and capable of communication with one another and/or other aspects of the system and present invention. Such sub-aspects may comprise an antenna 103, capable of both sending and receiving electromagnetic (e.g., microwave) and/or other radiation signals, which may be with the aid of an internal or external control system and power source. In some embodiments, received radiation (at either antenna 103 or otherwise), or a part thereof, may comprise the power source but, in others, a battery within device 101 provides the power source. In some embodiments, transceiver device 101 also may comprise a directional thermometer (such as an infrared thermometer) or pyrometer 105 as a sub-aspect, which may be directed toward at least a part of the user's body 101, for example, from the side of device 101 facing the user (into the page, in the perspective of the figure). Because all sub-aspects may be in communication with the control system, the control system may therefore take readings of the user's body temperature, which may, in a typical user, be approximately 98.2 degrees Fahrenheit, as a mean temperature, and 99.9 degrees Fahrenheit as an upper normal limit, although this figure may change (but remain correlated to average core body temperature) depending on the exact location of the measurements taken, and may also fluctuate throughout the day. For example, as pictured, if the thermometer/pyrometer 105 takes a reading of cutaneous and/or core body temperature from a user's chest, the readings may be significantly lower than core body temperature from other readings, but, nonetheless, a core body temperature may be correlated and extrapolated by the system based on the user's chest-based temperature data. In some embodiments, the correlation may be calibrated based on the mean or floating mean differential between a separately, substantially simultaneously measured core body temperature reading and readings from thermometer/pyrometer 105, but readings of great precision may not always be required to implement aspects of the invention.

Based on extrapolated core body temperatures and/or actual chest and/or cutaneous temperature readings, and in addition to other temperature or temperature-related radiation (e.g., infrared radiation) readings, aspects of the system may make useful relative temperature comparisons of nearby objects and the user's body (and/or the ambient temperature in the personal activity space, or beyond) to aid in activity recognition and analysis. In some embodiments, infra-red radiation readings may be taken from defined objects only, within a set distance, by imaging or otherwise directional temperature-related external infrared sensor(s) 107. The set distance may be variably set by the user and/or system, to define objects relevant to their physical activity, for example, by use of lenses or other selective or focal elements for focusing infra-red or other heat-related radiation emanating from such nearby objects. For example, in the figure, a focal and/or depth-of-field of the lens(es) may substantially render objects for object recognition, definition and analysis if they lie within a radius surrounding the device 101 or sensors 107 between 4 and 70 inches (for adult males), or smaller radii for children or women, for example, but such radii may be variably set by the user and/or system, and for different activity types and/or times of day as they occur or are recognized, on an ongoing basis. But preferably, the radius or other spatial and distance limit for object recognition, definition and tracking is sufficient to substantially include most personal activity-relevant objects for the user (thus defining a "personal activity space"), while eliminating recognition, definition and tracking of from more distant objects, or, at least, placing them in a different category for activity-relevant analysis, such as those factors defining a more general venue relevant to the user's activity, rather than being included as movement directly caused by the user's activity. Preferably, at least two infrared sensors 107 are used, to aid in object location in three-dimensional space, but three such sensors are preferred, to simplify 3-D object definition and location in space. A single sensor may also be used, however, in some embodiments.

At least one exemplary tracked, defined and analyzed moving object is depicted in the figure: namely, a burger 109. As shown in the figure, the core temperature of burger 109 is, at the time depicted, 189 degrees Fahrenheit. As such, the sensors 107 may, for example, recognized the burger 109 as an object with a temperature substantially heightened from the core temperature of the user, with boundaries between 5 and 10 inches away from the device 101 and/or sensors 107 and, depending upon the embodiment, may further define the size of the object and likely matches for the object. As the user begins to consume the burger, the device and sensors may track the burger 109's movement as an object, as it is carried into different positions, acceleration and movement vectors (or patterns thereof) relative to the user 100, device 101 and sensors 107 (for example, arcing toward the user's mouth, above the device 101 and sensors 107). That sensed data may then be delivered to a CPU or other control system for storage and further analysis by the system. An exemplary control system is discussed in greater detail below, in reference to FIG. 7.

Based on a wide variety of possible object recognition, definition and tracking algorithms, each of which fall within the scope of the invention, but do not limit it, the control system may determine that, based on the shape, size, temperature, temperature loss and loss rate, movement, other activity and other sensed and recorded factors, that the user is likely consuming a burger, and may further determine the burger's type based on a library of profile data for each such factor recorded. This recognition activity may be enhanced at the time, and enhanced in future object and activity tracking (by adjusting object and activity-recognition library factors recorded for the object or activity) by the user indicating to the system, using a separate GUI, the nature of her activity at the relevant time —which indications may be carried out simultaneously, or at a different time, and may be conducted (but need not be) on a GUI of another device (for example, on a PDA), networked to the system, with specialized software and hardware for presenting, communicating with and controlling such a GUI.

Furthermore, the control system, with the aid of sensor data, may determine the change in size of the object, or transfer of part of the object to a different, relevant location, such as the user's mouth and/or throat. The system may take such attrition in the object to correlate with object consumption and, based on such activity, maintain a count of likely calories, vitamins, protein and other nutritional information, as consumed by the user, in aid of other data storage, analysis and software presentations on computer hardware. Some such consumption information may be gathered by direct sensation, for example, by a swallowed or implanted sensor in communication with the system, present or scanning at least a part of the user's digestive tract, and determining the presence of food products, digestive products, enzymes, bowel sounds, and other indicators of digestive activity. Alternatively, digestive activity itself may be inferred by secondary, sensed data. For example, a pattern of body temperature increase may be correlated by the system with a conclusion that the user is or may be consuming different types and amounts of food, with different caloric and other nutritional and other properties. As another example, a user and or a system element, such as transceiver 101, may take a photograph of an object to match it with a food type and assess its size, caloric value and other nutritional profile, through photographic object-recognition. As still another example, nearby beacons (but outside of the user's personal activity area) may send signals relevant to the user's general environment and activity that may be relevant to identifying the user's objects in her personal activity space, as will be discussed in greater detail below. Generally, any technique set forth in this application may be blended, factorially applied, or otherwise combined with other (extant or new) object and activity pattern recognition techniques, to improve the accuracy of each technique.

The form of sensor/transceiver device 101, although preferred, is by no means exhaustive of the myriad devices and device locations that may be used as discussed above. In some embodiments, a wristband, armband or other belt or sticker may be used. In others, an implanted or skin adherent version may be used, rather than a necklace form, as pictured. In some embodiments, a conventional PDA device, or other device, with all or part of a specialized sensor/monitor set or device, as discussed above, may be used for all or some of the sensing aspects discussed above. Some alternate forms of such a sensor/monitor set or device are discussed in greater detail, for example, with reference to FIGS. 2 and 3, below. As another possibility, but again not exhaustive, the sensors and system aspects within device 101 may be consolidated with other aspects, or may be separated, in a place peripheral to the person. In that instance, distance calculations may be inferred from relative distances from both the user and other recognized objects, and rather than from sensors on a device or the device itself, exclusively. A local tag held on the person, however, such as the tags discussed in greater detail below, may also be used in such embodiments to aid in locating and defining the user and his/her relevant personal activities. It should also be noted that the sensor types and number(s) discussed with reference to this figure are not exhaustive of the possibilities that may be used to carry out aspects of the present invention. For example, in some embodiments, accelerometers, GPS or other local movement-defining systems, and tracking tags (which may be active or passive in generating signals), as discussed below, may also be used to aid in recognition of the user's personal activities.

In addition to object, motion and activity definition and tracking aspects set forth above, the system may extrapolate a wide variety of additional relevant, activity and other health-related data to enrich its resources relative to a user' account on the system. For example, sensors 107, or other sensors, in a device such as 101 may sense heat flux (influx and efflux across the surface of the user's body) to determine or approximate the amount of heat energy currently being lost by a user, to make caloric loss inferences as well as aid in defining a user's activity level. Similarly, humidity sensors and meters for ambient and user-transpiration-caused humidity, and galvanic resistance sensors, inferring sweat and other evaporative heat loss as well as radiative heat loss, may be included in device 101, to aid, among other things, in defining the user's exertion level and/or heat stress, as well as caloric energy loss (and compare it to food and drink caloric consumption information, and losses caused by exercise that is non-redundant with that loss, to determine a complete caloric profile). With data from such sensors indicating higher-than-average calorie burning by the individual, and within a range associated by the system with greater exertion, such as high-cardiovascular-impact exercise, the system may implement an algorithm making determination that the user is presently exercising, and may further record and analyze that conclusion for later purposes. As another example, additional sensors on device 101 may take an ambient temperature, to better estimate the user's heat differential (and stress) with respect to his or her environment.

Some sensor methods may be newly-blended to obtain better results. For example, active irradiation and reception for ranging, location, collocation and tracking of objects may also, as reflected back, indicate other conditions of the user, as with infrared irradiation and radiation, which, based on differences in intensity from reflection, reabsorption and resulting efference from the object, also may indicate temperature(s) of the object. In addition, a new form of differentiated radar, sonar or other reflective radiation tracking, where angular ranges of efferent radiation are sent with signature coding, and reception back may aid the system in determining whether a signal has been reflected multiple times or has otherwise been scattered, to more highly resolve object, its contours in space, and object activity maps and patterns by inferring 3-dimensional repeated reflection (and surface angle) information.

The device 101 may contain blood pressure monitors, ECG contacts, heart-rate monitors, a breathing-rate monitor, air quality and V02 sensors on or about the user, other internal or external bodily activity monitors (which may be with the aid of internal sensors indicating the status of internal bodily operations) and other health and vitals monitoring sensors and gears for recording, transferring and analyzing such information to the system.

Figure 2:
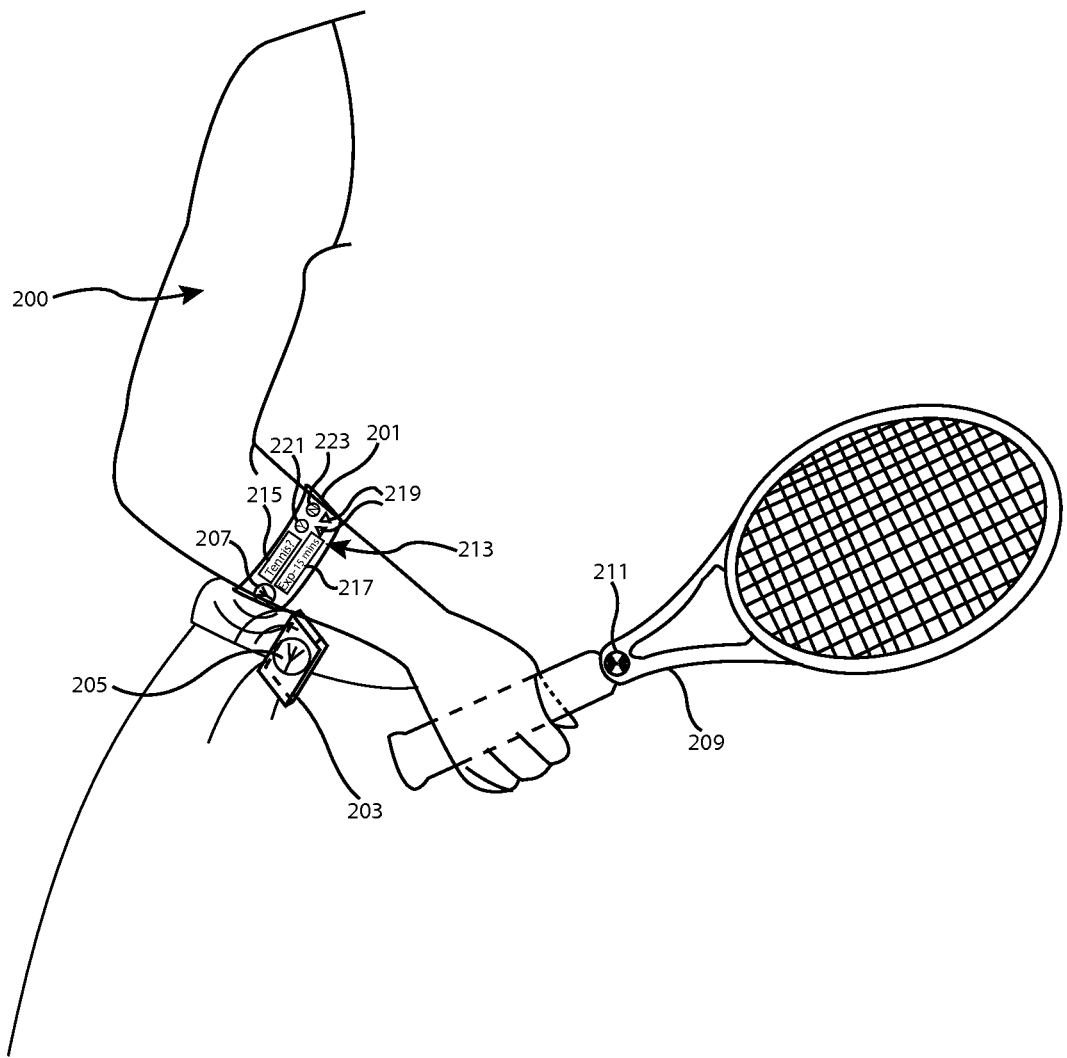
FIG. 2 depicts an alternate form of personal activity defining, tracking and analyzing device used in conjunction with a second sensor set, which may track one another, in addition to recognizing, defining, tracking and analyzing objects, in aid of personal activity definition and analysis by a system.

FIG. 2 depicts an alternate form of personal activity defining, tracking and analyzing device 201, used in conjunction with a second sensor set 203, which may track one another, in addition to recognizing, defining, tracking and analyzing objects, in aid of personal activity definition and analysis by a system. As with device 101 and its sensors 107 from FIG. 1, above, each device 201 and 203 is located on or about a user's body, 200. But, as should be understood with respect to FIG. 1, a wide variety of alternate locations, on or about a user's body, clothing or personal effects, may, alternatively, or in addition, be used. Also as with device 101, either device 201 or 203 may include a set of infra-red and/or other sensors, capable of carrying out but restricting types of object recognition to a relevant radius from the sensors (not specifically pictured). In addition, one or both devices 201 and 203 may include accelerometers, GPS or other local movement-defining systems, and trackable tag(s) or transmitting, receiving or transceiving antennas, such as those pictured as antennas 205 and 207. Antennae 205 and 207, among other things, may sense the relative position, distance, movement, acceleration (and patterns thereof) between one another, to assist in assessing the personal activity of the user, by delivering such data to a CPU or other control system for storage and further analysis by the system, including, but not limited to, personal activity definition and analysis. By using such multiple devices 203 and 201, with such sensor arrays, and with defined relative position, speed and acceleration data, the system may, in some embodiments, better define personal activity than with one device and sensor array, although the cost may also be greater.

As an example, the user in FIG. 2 is currently engaging in a sporting personal activity—namely, playing tennis. As such, she is holding a tennis racket 209 in her right hand, which is the same hand on which she wears device 201 (preferably her dominant hand). Each device 201 and 203 may then track the tennis racket 209 as an object within their focal radii (depth-of-field of their infra-red sensors' lenses) and, in conjunction with their relative physical data, better define the location, size, shape, movements and other characteristics of the racket from multiple angles. In such an embodiment, the sensors on each device 201 and 205 may be made fewer on each device, and a single rather than multiple infrared sensors may, for instance, be used due to the multiple locations of the two devices, 201 and 203. Lensing may also be omitted in favor of the system analyzing varying angle, orientation and positional data from the two devices, 201 and 205, to define and analyze objects from simpler (e.g., range only) data. In any event, as with the single device discussed with reference to FIG. 1, the multiple devices 201 and 205 may determine that the temperature of the racket 209 from which infrared radiation is emanating is substantially below the user's core body temperature. From this, the system may infer that a moving object within the user's personal activity space (or radii) defined by the depth-of-field or variably set distance parameter, is shaped like a racket and an inanimate object that has not been, for example, recently cooked for consumption, unlike the foodstuff object discussed in FIG. 1. From these data, delivered to a control sub-system of the system (such as the control system discussed with reference to FIG. 7, below, and other pattern and object matching, the system may determine that the user is presently engaging in the personal activity of playing tennis. Further data, for example, related to patterns of relative movement between the two devices 201's and 203's sensors, other sensors, and/or accelerometers, may also be delivered to the control system and further aid the system in determining activity levels (e.g., intensity of exercise) likely calories burned, cardiovascular impact, and other analytical outcomes. Such additional sensors may include, for example, other local tags, for example, tag 211, placed on the racket by a user of the system. Such tags, if placed, may define objects on which they are placed and transmit data to the system (for example, via one of the devices 201 and 203, which may include and/or be networked to a control system. As with the antennas 205 and 207 of devices 201 and 203, from such transmitted data from tag 211, a control system may determine the range or more complex movement data for the tagged object, as well as it's identity and orientation, to aid in activity pattern matching, definition and further analysis. In some aspects of the invention, a user may assign identities and types to a form of tag with uniquely-identifiable transmissions (in comparison to other tags) from a library of possible object types within the system (which may be expanded by the user and/or system, as can a similar library of possible activity types and intensity levels), and the proper orientation of the tags may be correlated with the position of the object on which it is placed, either by user-definition and/or calibration routines, or by orientation instructions from the system to the user (e.g. what location and orientation to place the tag on the object, based on its definition). For example, such tags may have unique, coded reactions to external radiation pings, for example, transmitted from one or both of the devices 201 or 203, such as resonant or partially absorbed vibrations or re-transmissions of such pings to the device(s) 201 or 203, which then may recognize the tag, and associated, defined object currently within the personal activity space of the user, and its movements, and extrapolate other analysis therefrom.

As mentioned above, to further aid the system in recognizing, defining, recording and analyzing personal activity, a user may utilize a GUI, which may be presented on one of the devices 201 and/or 203. Such a GUI is depicted as GUI 213, on device 201. GUI 213 may include display element(s), areas or element orders, such as 215 and 217, and user-actuable controls, such as exemplary scroll arrows 219, and "yes" or "no" input buttons 221 and 223. Display 215 may, among other things, and as pictured, display the system's current evaluation of the present personal activity of the user. In the instance of the figure, for example, the system may have determined, through the data sources discussed above, and applying matching profile libraries, that the user is most likely currently playing tennis. The user may therefore view this analytical conclusion on element 215 and, if she agrees, indicate to the system that she is, in fact, undertaking the assessed activity by actuating "yes" button 221, next to it. If, however, the system's assessment is wrong, she may so indicate by actuating the "no" button 223. After that, another displayed message, such as the system's next best guess for activity, may be offered. The system may take such input from a GUI from the user and, based on alterations to system-alterable algorithms, define or improve its definition of the user's activity, and the resulting influence of that activity definition on calorie burning, cardiovascular impact, and other analyses for the user's personal activity. Display element 217 may display additional (possibly secondary), relevant information to the user relevant to his or her personal activity, and such as (as pictured) the amount of time that the system has determined has been spent performing the currently assessed activity type (i.e., playing tennis). In some embodiments, the user may actuate a GUI control to set the start and end points of new activities and make other commands, such as selecting a displayed, actuable GUI aspect (not pictured) and the user may scroll through various displayed data, using scroll controls 219.

The types of data input and output and user controls set forth above are exemplary only, and any form of user setting and/or control necessary or possible by a user, as set forth in this application, may be carried out in alternate GUIs, GUI-providing or other device(s), and/or sensor(s) or set(s) thereof, which may be used alternatively, or in addition to the GUI and sensor examples discussed above. In addition, any other personal activity- or other health-relevant data may be entered and transmitted to the system for processing, in other embodiments of the invention—not just personal activity types and durations, as discussed specifically above. For example, a user and/or system may gather, identify, track, record and analyze data concerning eating behavior, sleep activity and patterns and compliance with medical regimens, among myriad other possibilities.

Figure 3:
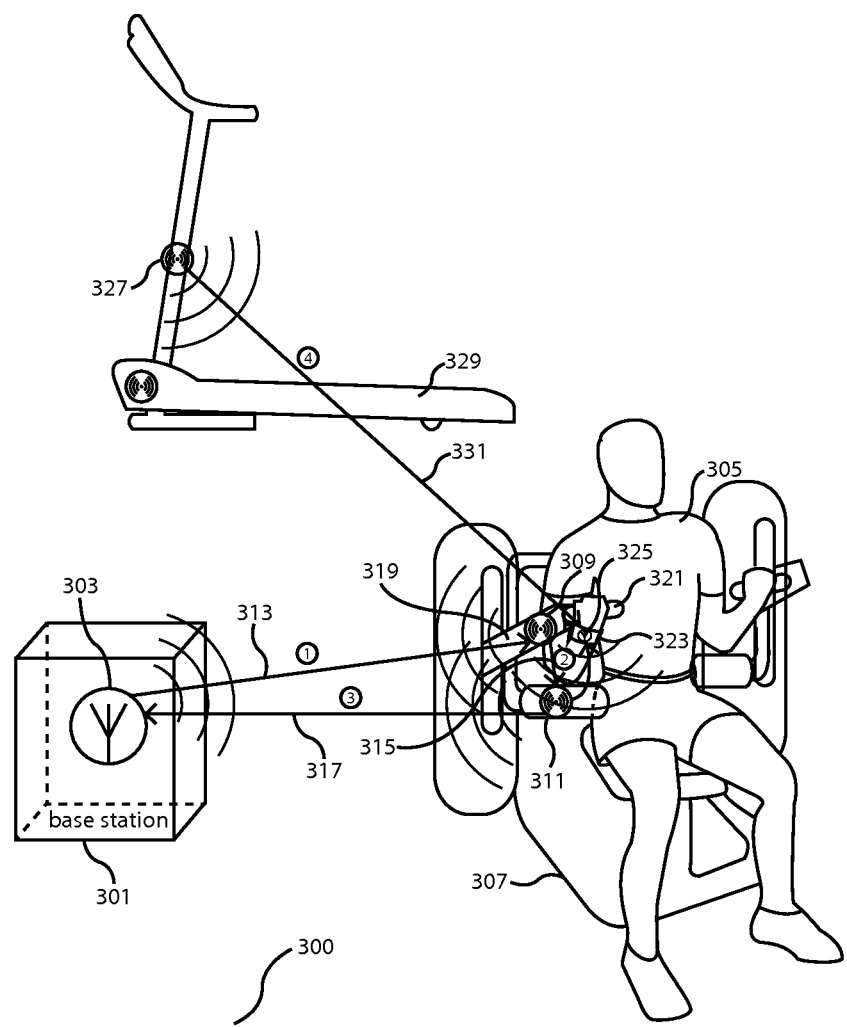
FIG. 3 depicts a personal activity defining, tracking and analyzing base station, used in conjunction with specialized sensor tags by a system to identify, define, track and analyze personal activity, in accordance with aspects of the present invention.

FIG. 3 depicts a personal activity defining, tracking and analyzing base station 301, used in conjunction with specialized sensor tags by a system to identify, define, track and analyze personal activity, in accordance with aspects of the present invention. The base station 301 may comprise or be networked with a control system, such as the exemplary control system discussed with reference to FIG. 7, below, and further comprises communications capability and, preferably, wireless communications and power-providing capability, such as transceiver antenna 303. Also preferably, base station 301 is placed in an area near, but outside of the personal activity space used by a user, whose activity is identified, defined, tracked and analyzed by the system. Even more preferably, base station 301 is placed near enough to a personal activity space that communications will be possible with tags placed on or about the personal activity space, but does not physically interfere with that personal activity space, or the depth-of-field or other personal activity space or radii otherwise defined by the user and/or system.

A user 305 is pictured in a seated position, performing bicep curls on a bicep curl machine 307. Within, on or about the machine 307, and also within the user 305's personal activity space, are specialized tags 309 and 311, each of which is unique and capable of receiving a radiated signal and, as a result, transmitting a somewhat weaker resonant signal with unique identification properties indicating from which tag it originated. For example, the base station may send an initial signal 313, for example in a pulse or burst format, at a frequency with which tag 309 resonates and, as a result, next produces its own unique resulting (and uniquely resulting from the nature of the signal it received) signal 315. Next, tag 311 receives signal 315 and, owing to its properties, may resonate with that signal and produce its own unique resulting (and uniquely resulting from the nature of the signal it received) signal 317, which may then be received by the base station. Although directional lines are shown for each of the signals, to demonstrate where they are received, they may not be directional in nature. In fact, each resulting signal from a tag loses substantial strength in comparison to its source signal, from which it radiates, as it radiates outward and due to energy losses in the resonant process. But, in any condition of the equipment and ambient environment, including with interceding bodies between the base station and tag 311 (or 309 if it, instead, is used as the final tag in the signal chain, in another embodiment), the final resulting signal 317 is strong and complete enough that the base station is capable of receiving, processing identifying and analyzing it. The unique reaction to unique signals of each tag may be by the resonant properties of the tag (which may be multi-variate and react to unique frequency patterns and other coding) may be due to the properties of a resonant material, selective absorption and reflection, or from active modulation (for example, with the aid of a local processor on board each tag).

As the user 305 performs bicep curls on machine 307, a lever 319 attached to curling bar handles 321 may variably rise upward (on the user's bicep flexion) and downward (on the user's arm extension by relaxing his biceps). Tag 309 has been placed within, on or about lever 319 and, as a result, will rise upward and downward along with the movements of lever 319. Tag 311, by contrast, is placed within, on or about a fixed part of machine 307 relative to the floor 300 and majority of machine 307 and user 305, and, therefore, tag 309 will move relative to tag 311 as the user 305 performs the bicep curl exercise. Because each of tags 309 and 311 receives a signal (313 and 315, respectively) that has experienced power attrition over the course of its travel, and because the power attrition of signal 315 as it reaches tag 311 will vary based on the variable distance between tags 309 and 311, the strength of the resonation or other harmonic or other resulting unique signal 317 will itself vary based on the position of lever 319. In addition, the change in signal strength will directly and proportionately relate to the change in distance between the stationary and moving tag pair, making movement tracking easier to accomplish, with less variables, than with ordinary object position tracking. In some embodiments, the nature of the final, efferent signal from a tag to the base station may vary in a character other than strength, however, in reaction to receiving different strength signals, to accomplish the same movement tracking objective. From this, over time, the base station 301 may analyze the variation in signal strength (or other, distance-variable properties, in other embodiments) of signal 317 to infer when exercise is occurring on the machine. Likewise, a PDA or other system element 323 on or about the user (e.g., a wrist-mounted device, as pictured) may also receive signal 317 with an antenna 325, since it need not be directional, and perform the same hardware and software steps to determine that the exercise is taking place, the number of repetitions of the exercise, and the amount of time spent performing the exercise, or may directly communicate with the base station to receive that information and/or identify the user performing the exercise, for example, by assessing that the machine's tags 309 and 311 are on or about the user 305's personal activity space. Likewise, the base station may ping the user's device 323, to locate it, or co-locate it with the machine in the same way as with the lever 319, and establish his identity as the user of the machine. Other tags defining other machine movements may further aid the system in assessing personal activity information. For example, additional unique signal-generating tags (not pictured) may be placed on weight plates, to identify the amount of weight used, based on their movement and/or location relative to fixed tag 311, in accomplishing the exercise repetitions. In an environment with several tagged machines, such as a gym using the system, the base station may emit different resonant frequencies to which each initial tag, such as tag 309, responds, and leading to unique resonant frequencies to which each second resonating tag, such as 311, responds. Alternatively, the system may differentiate between resonating frequencies that are too weak to correspond with resonation caused between co-located tags on one machine, and disregard them as indicators of personal activity. For example, if the same initial signal 313 reaches an initial receiving tag 327 on a treadmill 329, and which then sends a fourth resulting resonant signal 331, the system and/or the user's device 323, may disregard that signal as too distant in origin to correspond with that user's location. However, such signals emanating from neighboring personal activity spaces of others may still be used, for example, to aid in defining the user's environment and, secondarily, his activities.

Figure 4:
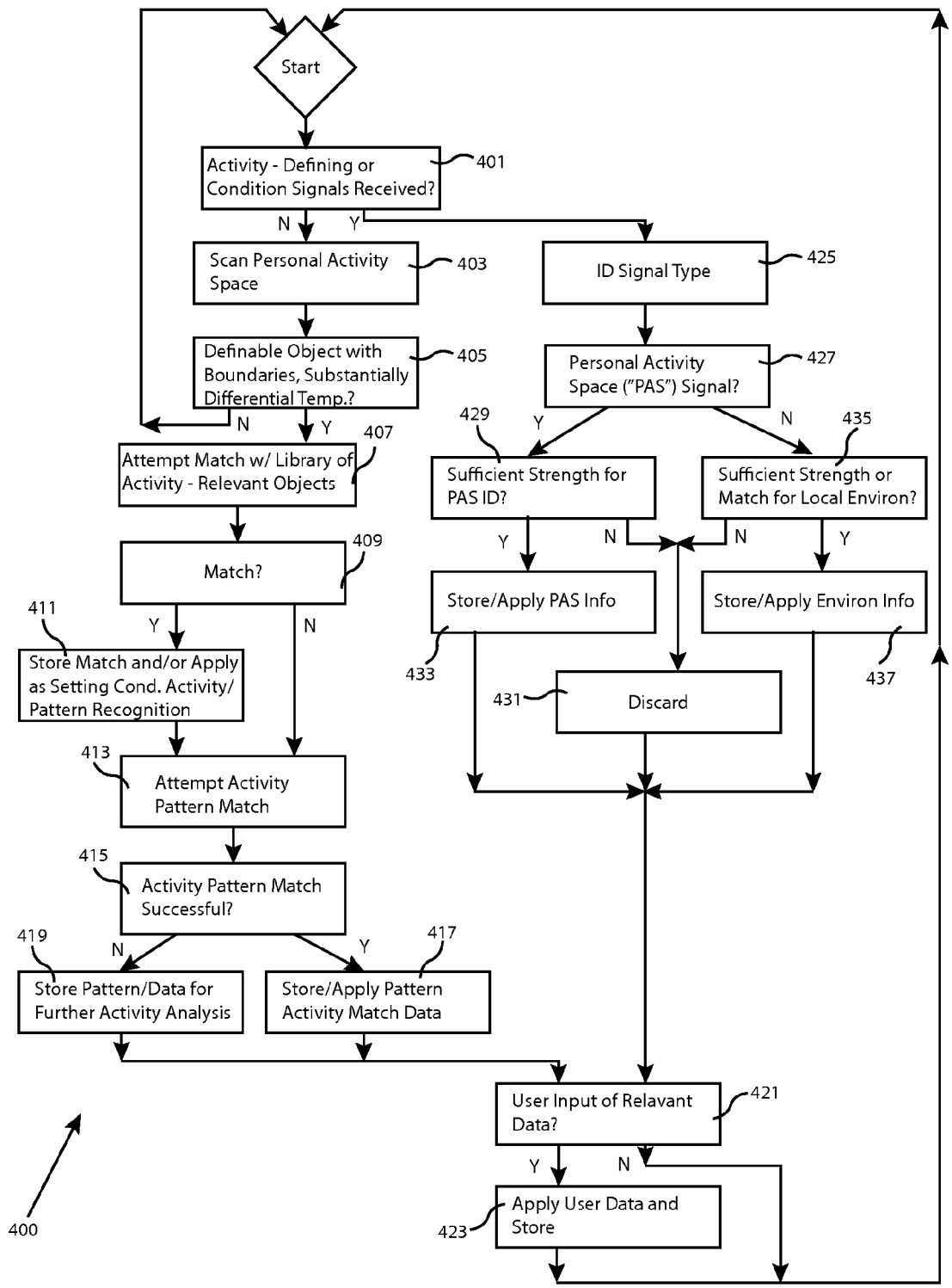
FIG. 4 is an exemplary process flow diagram of exemplary steps that may be taken by a system, such as (but not limited to) a hardware and software control system, for example, of the nature discussed with reference to FIG. 7, implementing aspects of the present invention.
Figure 7:
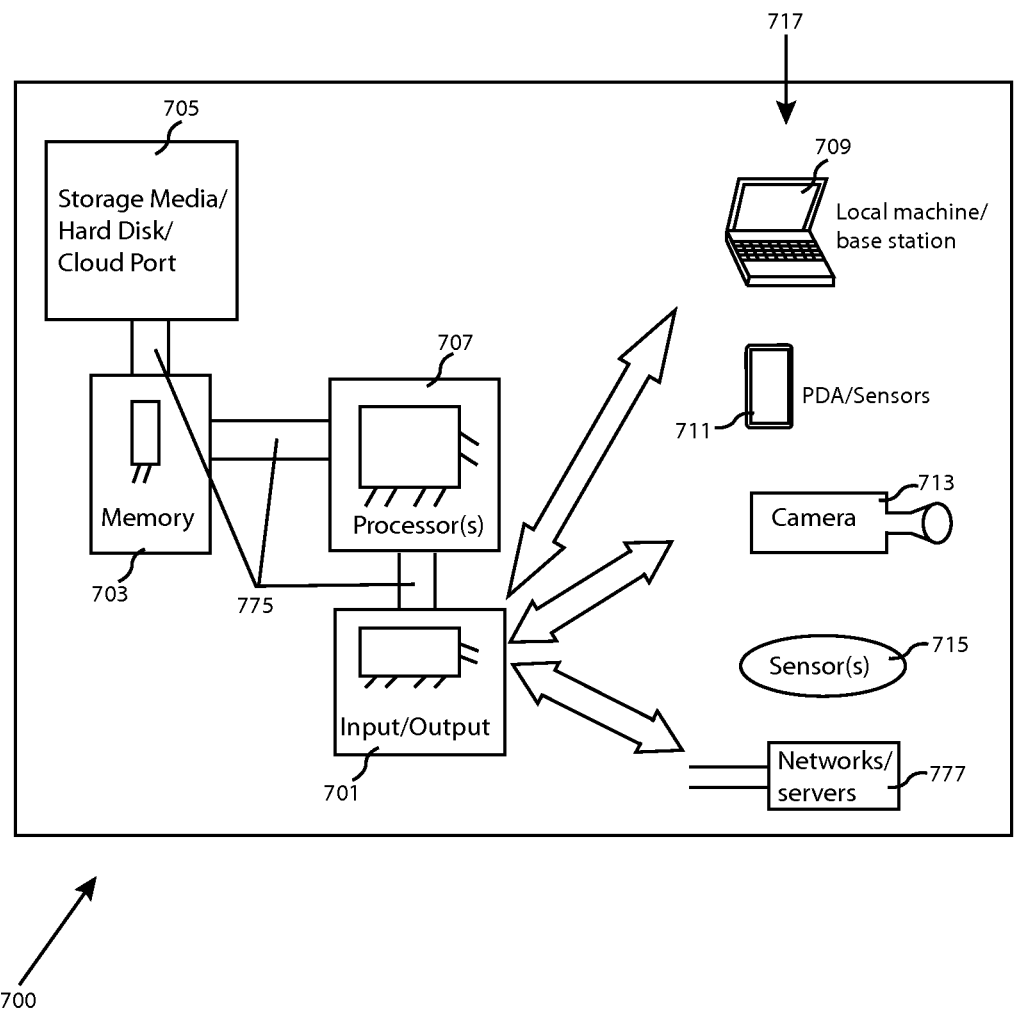
FIG. 7 is a schematic block diagram of some elements of an exemplary control system that may be used in accordance with aspects of the present invention.

FIG. 4 is an exemplary process flow diagram of exemplary steps 400 that may be taken by a system, such as (but not limited to) a hardware and software control system of the nature discussed, for example, with reference to FIG. 7, implementing aspects of the present invention, and which may be a part of a larger personal activity monitoring and analysis system.

Beginning in step 401, the control system first determines whether Activity-defining or -condition signals have been received by the control system. Such signals may come in a multitude of forms, as discussed further below, and elsewhere in this application, and may assist the control system in determining a type, amount, nature, direction, frequency, duration, and intensity of personal activity(ies) that are, have or may occur with respect to a user whose personal activity is being tracked by the system. If no such new signals are currently being received, however, the control system may proceed to step 403, in which it may cause transceiver(s) to detect radiation (of any type) to test the local environment (specifically, the user's variably definable personal activity space), for example, with radar, sonar, or infrared object recognition, definition, tracking imaging, analysis and/or ranging, as discussed elsewhere in this application. Following this, the system may next determine whether there is a definable object, apart from the user's body (as well as, in some embodiments, extensions of the user's body, such as arms and legs, the activities of which may also be tracked) by assessing a significant difference in temperature between such object(s) and the user's core body temperature, in step 405. If no such object is found, or tracked as moving, in the instance of embodiments tracking the user's body movement, the system returns to the starting position. If, however, the system does so define an object, it may next attempt to match it—for example, by shape, temperature, size, motion and/or other physical characteristics—with profiles of such characteristics for objects and object types from a library accessible and so comparable by the system, in step 407. If such an object match, or type of object match is made by the system (for example, within a confidence interval which may be variably set by the user) in step 409, the system may proceed, in step 411, to record the match and/or apply it as a setting or condition influencing further activity and/or activity pattern recognition. For example, to extend the example provided in FIG. 2, if the system identifies an object in a user's hand as a tennis racket for a given duration, the system may store that fact for later use, and create and apply an influential factor in its current pattern recognition analysis based on that match. For that duration of time, for example, swinging movements of the user's arm that might otherwise have been interpreted as other movements are more likely to be identified as tennis playing activity, due to that new factor taken from object recognition in the user's personal activity space. Similarly, if an object in the user's hand is identified as a burger, as in FIG. 1, that fact may be converted into a factor making eating activity more likely, and more likely to be recognized by a user's hand and head activity than otherwise might be the case (rather than, for example, the user's hand movement towards her face being interpreted as more likely an activity of blowing her nose, absent the object recognition of the burger). In any event, the control system next proceeds, in step 413, to attempt to perform personal activity pattern matching, from any movement perceived in the user's personal, again, with a library accessible to the control system—this time, a library of movements, accelerations, postures and other indicators of personal activity status. This activity pattern matching may be aided by sensors or other activity-monitoring data sources providing data to the system, such as accelerometers and/or GPS sub-systems, and by recognized object movement of objects that themselves have not been defined by the system (for example, if no match is achieved in step 409, also leading to step 413). Next, if an activity pattern match is achieved by the system in step 415 (for example, again, within a variably set confidence interval for matching), the system again may store data relating to that match and/or use that match as a factor influencing its further personal activity monitoring activities and analysis, in step 417. But even if no such activity pattern match is not achieved, the system may nonetheless store and analyze the unmatched data, for example, to determine likely calories burned, cardiovascular intensity and impact, and other outcomes of personal activity, based on default or general functions applied by the system, in step 419.

Next, the system may proceed, in step 421, to determine whether a user has input further, relevant information—for example, utilizing a GUI of a type such as that discussed with reference to FIG. 2, above. If so, the system may both store and apply such data, as indicated with reference to that figure, in step 423.

If, returning to step 401, the system instead determines that activity-defining or -condition signals (designed and programmed for assisting the system in that regard) have been received by the control system, the system may proceed, in step 425, to determine the nature of the signal—such as its radiative type, frequency and any encoding—to determine which type of signal(s) for assisting the system it is. First, the system may determine whether the signal(s) is a Personal Activity Space ("PAS") signal—meaning that it is of a type used by the system to indicate activities within a user's personal activity space—in step 427. For example, the types of resonant signal examples emanating from tag(s) provided in reference to FIG. 3, above, are PAS signals, because they originate from and directly indicate activity within the user's personal activity space. Next, if such a PAS signal is detected, the system may proceed, in step 429, to determine whether that PAS signal is of a sufficient strength to originate within the user's personal activity space. If not, the system disregards and may discards data regarding the signal, as emanating from another person's personal activity space, in step 431. However, in some aspects of the invention, and embodiments, a PAS signal originating from beyond the user's personal activity space may nonetheless be used by the system as an environmental condition indicator, which may influence the system's algorithms and personal activity matching and analysis, as other such factors so influence the system, as discussed above. If the PAS signal is of sufficient strength that the system determines it to directly indicate the user's personal activities, however, in step 429, the system proceeds, in step 433, to store and apply data corresponding with that signal in its personal activity analysis, and other actions based on that analysis, as discussed further herein. The system may then proceed to steps 421 et seq., as discussed above, and, then, to the starting position. If, at step 427, the system determines that the signal received is not a PAS signal, it may next determine, in step 435, whether the signal is of a sufficient strength to originate in, about or near the user's local environment, such that it may be relevant in defining the user's potential personal activities. The sufficient strength and distance of origin to render that determination may, as all factors discussed in this application, be variably set by the user and/or system. If it is of such sufficient strength, the system may store and apply data relating to that determination as a factor influencing its determination, definition, recording, matching and analysis of further personal activities. For example, if a local signal (for example, from a transmitter of a shopping mall) is sufficiently strong and local to indicate that the user is present in the shopping environment, a bag, hand-swinging of the bag, and article movement will more likely be interpreted by the system as of a shopping personal activity nature, rather than, for example, croquet, even if, otherwise, the arm movement might slightly more greatly match a hand movement profile stored in the library as relating to croquet, than one relating to shopping.

Figure 5:
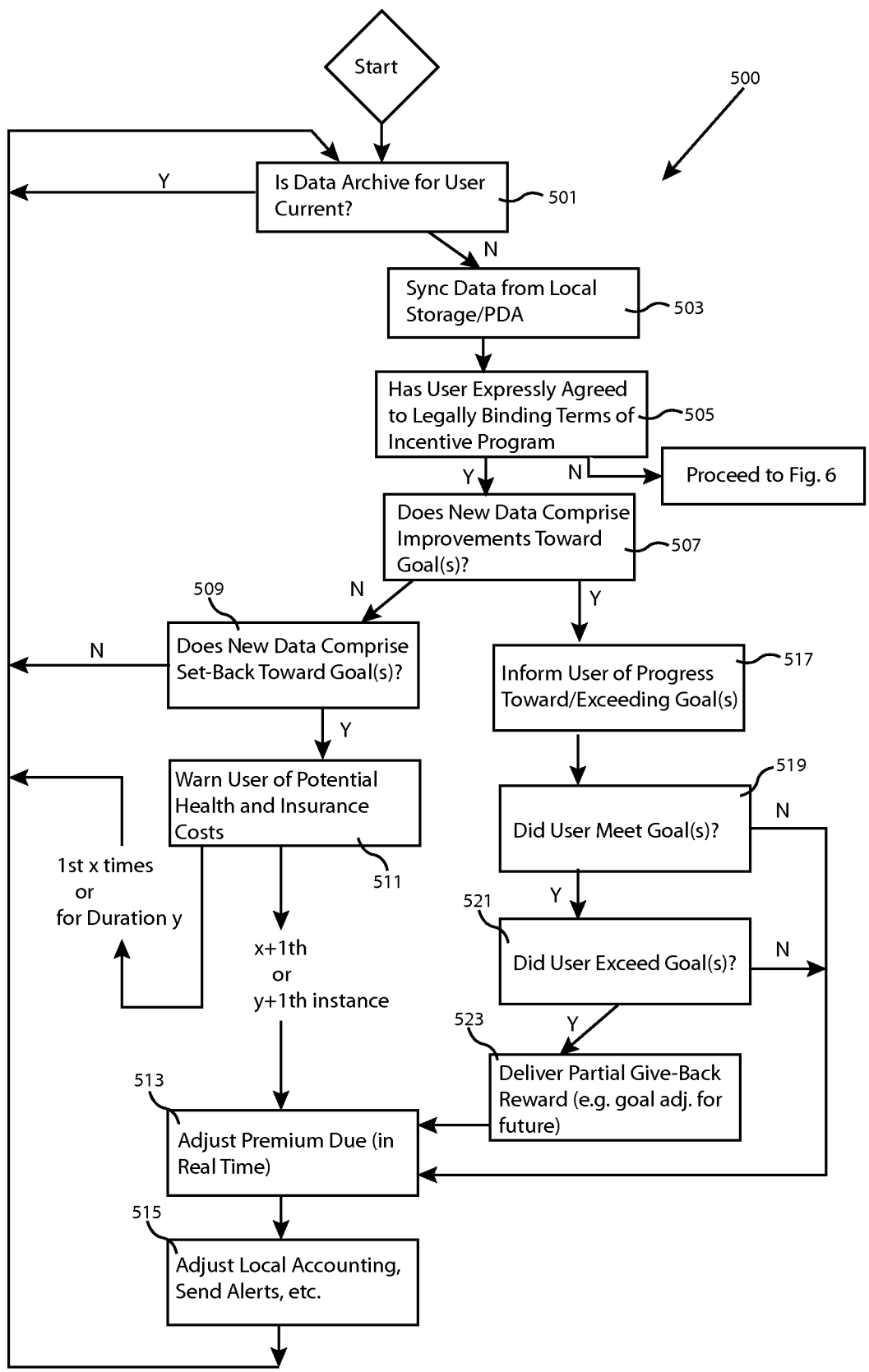
FIG. 5 is another exemplary process flow diagram of exemplary steps that may be taken by a system, such as (but not limited to) a hardware and software control system, for example, of the nature discussed with reference to FIG. 7, implementing aspects of the present invention.

FIG. 5 is another exemplary process flow diagram of exemplary steps 500 that may be taken by a system, such as (but not limited to) a hardware and software control system of the nature discussed with reference to FIG. 7, implementing aspects of the present invention. The exemplary steps may be undertaken by such a control system to govern aspects of a larger personal activity and health data tracking system, comprising the control system. In particular, with respect to the steps set forth with respect to this figure, the system may implement goal achievement or underachievement rewards and penalties, and administer legally-binding agreements regarding the same between tracked and other incentivizing, insuring users. The series of steps 500 undertaken as set forth in this figure may be undertaken periodically, for example, according to an agreed schedule, or may be undertaken on an ongoing, real-time basis, based on when new, relevant data is received by the system, or substantial amounts or other trigger amounts and/or types of such data, are taken in.

Beginning with step 501, the control system first assesses whether a current archive data storage device, preferably in the immediate and ongoing control of the control system (such as memory device 703 or 705, discussed in reference to FIG. 7, below) has been updated to contain the latest substantial or other significant amount or type of data relevant to a user's personal activities, from the remainder of the tracking system—for example, from storage on a PDA's local drive. If so, the control system may return to the starting position. If not, however, the control system proceeds, in step 503, to import, or copy and import, those data for local storage more immediately and controllably accessible and modifiable by the control system ("Syncing" the data), and for further processing and analysis. In step 505, the system assesses whether the user has expressly agreed to the terms of use of the control system sub-services implementing incentives, as set forth in subsequent steps of the figure. If not, the control system proceeds to the first step of FIG. 6, below. If so, however, the control system proceeds to step 507, in which it may determine whether the data represents personal activity that constitutes improvement(s) towards goal(s). Such goal(s) may be variably set by the system and/or a user, according to input by at least one user and/or the system, or by agreement between users (such as a tracked user and control system administrative user, with the authority to set and deliver incentives). If the data does not reflect an improvement towards a goal, the control system proceeds to step 509, in which it determines if the data reflects a set-back, or worsened state of personal activity in comparison to such goal(s). If so, the control system may proceed to step 511, in which it warns the user with a message (for example, delivered on the user's PDA based on network communications) warning the user of potential health and other costs of their personal activity status, in moving away from the user's set goals. Depending on the embodiment of the invention, if such warnings occur more than a preset number of times or recur for more than a permitted length of time, the system may proceed to adjust the user's insurance premiums upward, or take other negative incentive measures (e.g., increasing the costs of a gym membership, in step 513. Following such actions, the control system may undertake various accounting and other administrative steps recording and effecting relevant control system changes in light of the changed incentives, such as, but not limited to, alerting the user of the changes, or a healthcare provider of the user, or other peers that the user has agreed to alert, or increasing counseling or specialized healthcare visits in light of the failure to reach the goal(s), and the goal(s) may be redefined by user(s) and/or the system in light of the occurrence of the steps that have occurred. Following those actions, the control system may return to the starting point.

If, however, the system determines, back at step 507, that the Synced data represents personal activity that is progress towards, or that meets or exceeds, goal(s), the control system may proceed to step 517, in which it immediately reports that progress and/or other success to the user (for example, via network communication represented on the user's (whose personal activity is being tracked) PDA. Next, the control system may determine whether the user's personal activity met his or her personal activity goal(s), in step 519. If not, the system may proceed to steps 513 and 515, and carry out actions as discussed above with reference to those steps. If the user has at least met his or her personal activity goal(s), the control system may then proceed to step 521, in which it further determines whether the user's personal activity has exceeded his or her personal activity goals. If not, the control system again continues to steps 513 and 515 and carries out actions as discussed above with reference to those steps, but, in this instance, reflecting that the user has met his or her goal. Such actions may include delivering a promised positive reward (given as an incentive), such as lowering a user's premium cost for insurance, and alerts and notifications related to the same. If the user has, in fact, substantially exceeded his or her personal activity goal(s), the system may proceed, in step 523, in which it may deliver a special incentivizing reward, in which the amount by which the goal has been exceeded is partially awarded back to the user, for example, as a future goal adjustment. Such a technique for "Partial Give-Back" rewards is discussed in greater detail, below.

Among other incentivizing rewards and penalties contractually agreed to by a user, the system may set and issue penalties and rewards based on compliance with or exceeding a personal activity goal set by the system, which may be a goal set with the agreement, including, but not limited to the express written legally binding agreement. In some aspects, a reward for compliance and/or a penalty for non-compliance, per event or upon a count of a series of such goals, may include reduced or increased costs of fitness-related expenses or insurance coverage premiums. In other aspects, such rewards and penalties may be on a sliding scale, based on the degree of exceeding or underachieving relative to such goals, and future overachievement may remove the affect of previous underachievement, and vice versa. In a preferred embodiment, overachievement may create a reward of lower goal levels for future compliance, which may be only partial in comparison to the level of overachievement. For example, if a user has agreed to a system assessed goal of consuming 1800 calories per day, the system may reward a user who is assessed to have consumed 1600 calories only, in a given day, by rewarding that user with a partial give-back of 100 of the 200 calories overachieved, for a total caloric limit of 1900 calories for the following day. Such rewards may be phased out over time, to prevent licensing outright binge eating, for example. The term for such incentivizing rewards is a "Partial Give-Back" reward. Conversely, a partial-take-back penalty, in which a user's failure to meet a goal is partly reflected in future goal(s) may not preferred (to prevent a preferred incentive to cheat) and, instead, a complete assignment of the underachieved amount, or an even greater amount, is assigned to future goals. Generally, the system may implement a system of floating goals and rewards, to best achieve the user's longer-term objectives. For example, if a user's objective relates to increasing their muscle mass, while decreasing body fat, daily, weekly or other goals for food consumption and physical activity may vary based on the user's biorhythms, such as recent sleep quality, starvation-mode assessment (whereby the user's body begins to burn muscle, rather than fat, due to caloric consumption falling too low at a given point in the day), among any other possibility. The effect on consumption of different types of activities, and net calorie gains resulting, can be monitored by the system, and change the recommendations of the system. For example, the importance of at least some low-intensity exercise may be surprisingly emphasized in an algorithm applied by the associated control system, to offset the calorie-intake/hunger boosts of higher intensity exercise only.

In further aspects of the invention, the incentives may require no legal authority and meted out consequence to administer, but, rather, the system may simply offer observations that may incentivize the user as a natural consequence. For example, when the system warns a user of health consequences for deterioration in personal activity levels, or such levels that fall below advised levels for a user's age and other demographics, or personal situation, or when the user's other personal health-relevant data does not meet safe or desired levels, there may be a natural incentivizing effect. By communicating and illustrating likely outcomes and events (including, but not limited to, long-term outcomes) for personal activity and other health status data, the system may underscore such natural incentives.

Figure 6:
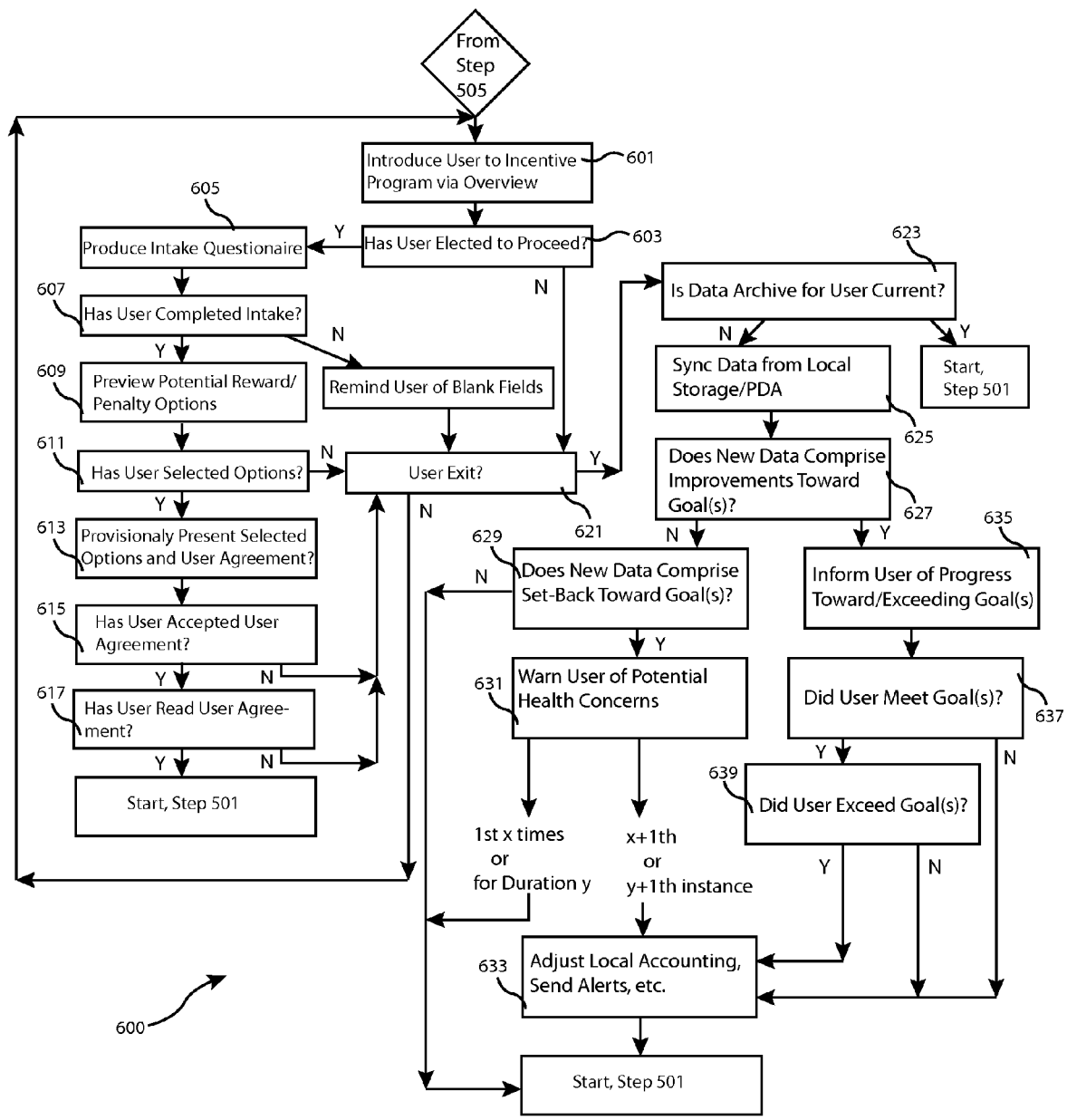
FIG. 6 is another exemplary process flow diagram of exemplary steps that may be taken by a system, such as (but not limited to) a hardware and software control system of the nature discussed with reference to FIG. 7, implementing additional aspects of the present invention.

FIG. 6 is another exemplary process flow diagram of exemplary steps 600 that may be taken by a system, such as (but not limited to) a hardware and software control system of the nature discussed with reference to FIG. 7, implementing additional aspects of the present invention. More specifically, in the event that a user of the system whose personal activity is being tracked has not yet set goals for personal activity, or legally agreed to participation in a contract or program incentivizing rewards and penalties ("Incentive Program"), as determined in step 505, above, the terms of which may be carried out as shown in the remainder of FIG. 5, above, the system may proceed to the steps set forth in this figure.

Beginning at step 601, the system proceeds to present the user with an overview of program aspects, for example, in the form of statements displayed on the user's PDA concerning the Incentive Program's goals, conditions and rewards and penalties, as well as other major terms and conditions to participation in the Incentive Program. If, after reviewing that overview, the user elects to proceed in step 603, the system may proceed to produce a questionnaire, in step 605, for gathering basic information necessary for the further administration of the Incentive Program (for example, user identity, age, occupation, proof thereof, credit card information for charging penalties, current personal activity and other health-related information, etc.). If the user has successfully completed the information requested in the intake questionnaire in step 607, the system may proceed, in step 609, to preview for the user a series of Incentive Program options, such as varying levels and types of goals for improving personal activity and activity levels, such as, but not limited to, exercise activities, medicine compliance and dietary intake —along with the potential rewards and penalties for meeting or failing to meet those goals. If the system determines that the user has accepted or selected certain of those options as goals, in step 611, the system may proceed to present those options as accepted options (provisionally) and further present the user with a full copy of an Incentive Program contract, dictating the entire understanding of the participating user and any person, business entity or other individual or organization responsible for and/or running the Incentive Program with the aid of the system (an "administrator") in step 613. The user to be subject to personal activity analysis then may formally accept that agreement, in step 615, or, if no longer interested (or at any other point) may exit in step 621, to use the system without the influence of the Incentive Program. If the user has accepted the agreement, but his or her failure to scroll through it, or specifically indicate that he or she has read the agreement (for example, in a check box) indicates that he or she may not have read through the entire agreement, the system may request that the user so read through every part of the agreement, and so indicate, in step 617. At that point, the user may be an active participant in the Incentive Program, and may return to step 501, to continue use of the system in that capacity.

If, however, the user has exited at step 621, at any point, the system may instead enter an operational mode for users who are not participating in the Incentive Program, at steps 623 et seq. Steps 623 et seq. are similar to steps described in reference to FIG. 5, but without provisions requiring legal participation in the Incentive Program. At step 623, as with step 501, the system assesses whether a current archive data storage device, preferably in the immediate and ongoing control of the control system (such as memory device 703 or 705, discussed in reference to FIG. 7, below) has been updated to contain the latest substantial or other significant amount or type of data relevant to a user's personal activities, from the remainder of the tracking system—for example, from storage on a PDA's local drive. If so, the control system may return to the starting position of FIG. 5. If not, however, the control system proceeds, in step 625, to import, or copy and import, those data for local storage more immediately and controllably accessible and modifiable by the control system ("Syncing" the data), and for further processing and analysis. The control system next proceeds to step 627, in which it may determine whether the data represents personal activity that constitutes improvement(s) (which may include improvement(s) towards goal(s) non-legally bindingly set by the user and/or system). Such goal(s) may be variably set by the system and/or a user, according to input by at least one user and/or the system, or by agreement between users (such as a tracked user and control system administrative user, with the authority to set and deliver incentives). If the data does not reflect an improvement towards a goal, the control system proceeds to step 629, in which it determines if the data reflects a set-back, or worsened state of personal activity in comparison to such goal(s). If so, the control system may proceed to step 631, in which it warns the user with a message (for example, delivered on the user's PDA based on network communications) warning the user of potential health and other costs of their personal activity status, in moving away from the user's set goals. Following such action, the control system may undertake various accounting and other administrative steps recording and effecting relevant control system changes in light of the changed incentives, such as, but not limited to, alerting the user of the changes, or a healthcare provider of the user, or other peers that the user has agreed to alert, or increasing counseling or specialized healthcare visits in light of the failure to reach the goal(s), and the goal(s) may be redefined by user(s) and/or the system in light of the occurrence of the steps that have occurred, in step 633. Following those actions, the control system may return to the starting point of FIG. 5.

If, however, the system determines, back at step 627, that the Synced data represents personal activity that is progress towards, or that meets or exceeds, goal(s), the control system may proceed to step 635, in which it immediately reports that progress and/or other success to the user (for example, via network communication represented on the user's (whose personal activity is being tracked) PDA. Next, the control system may determine whether the user's personal activity met his or her personal activity goal(s), in step 637. If not, the system may proceed to step 633, and carry out actions as discussed above with reference to that step. If the user has at least met his or her personal activity goal(s), the control system may then proceed to step 639, in which it further determines whether the user's personal activity has exceeded his or her personal activity goals. Regardless of whether or not the user exceeded his or her goals, the control system again continues to step 633 and carries out actions as discussed above with reference to that step, but, in this instance, reflecting that the user has met his or her goal or exceeded it. Such actions may include alerts and notifications related to the same.

The sequence and pathways, and exemplary steps themselves, as set forth in reference to FIGS. 4-6 are illustrative, and not exhaustive, of the many possibilities that fall within the scope of the invention.

FIG. 7 is a schematic block diagram of some elements of an exemplary control system 700 that may be used in accordance with aspects of the present invention, such as, but not limited to gathering data from sensor(s), sending alerts and other communications, sensing user or person's personal activity within personal activity space(s), provisioning user settings and permissions, presenting and recording legally binding agreements, and receiving control commands and managing input interfaces, such as, but not limited to a GUI, as defined and discussed elsewhere in this application. The generic and other components and aspects described herein are not exhaustive of the many different systems and variations, including a number of possible hardware aspects and machine-readable media that might be used, in accordance with the present invention. Rather, the system 700 is described to make clear how aspects may be implemented. Among other components, the system 700 includes an input/output device 701, a memory device 703, storage media and/or hard disk recorder and/or cloud storage port or connection device 705, and a processor or processors 707. The processor(s) 707 is (are) capable of receiving, interpreting, processing and manipulating signals and executing instructions for further processing and for output, pre-output or storage in and outside of the system. The processor(s) 707 may be general or multipurpose, single- or multi-threaded, and may have a single core or several processor cores, including, but not limited to, microprocessors. Among other things, the processor(s) 707 is/are capable of processing signals and instructions for the input/output device 701, to cause a display, light-affecting apparatus and/or other user interface with active physical controls (any of which may be comprised in a GUI) to be provided for use by a user on hardware, such as a personal computer monitor or PDA screen (including, but not limited to, monitors or touch- and gesture-actuable displays) or terminal monitor with a mouse and keyboard or other input hardware and presentation and input software (as in a software application GUI), and/or other physical controls.

For example, and with particular emphasis on the further aspects of the invention discussed in this application, in connection with FIGS. 1-6, the system may carry out any aspects of the present invention as necessary with associated hardware and using specialized software, including, but not limited to, application window presentation user interface aspects that may present a user with a software GUI for selecting properties, changing permissions for user and other person's entry, creating and changing settings for tracking, defining, identifying, analyzing and recording objects and personal activity, generating alerts and other communications, syncing data from local sources to more local and immediately controllable storage locations for the control system (such as memory 703 and storage media 705), data compiling and analysis, implementing incentive rewards and penalties and generally carrying out any control system steps set forth with reference to the remainder of the figures in this application. As another example, with reference to FIG. 2, such hardware and software may, with or without the presentation of options to a user for selection on a conventional display, carry out any control aspect of the invention as necessary and proper, such as, but not limited to interpreting, implementing and responding to user input for identifying activity types, and the timing of such activity, among other GUI entries, sending alerts, and other user interface and processing aspects that may be used in the art, such as physics engines, physical modeling, detection, internet or other network protocols and encryption, image-creation, recording and remote or local (such as wired or physical interface) control (and related software).

The processor 707 is capable of processing instructions stored in memory devices 703 and/or 705 (and/or ROM or RAM), and may communicate with any of these, and/or any other connected component, via system buses 775. Input/ output device 701 is capable of input/output operations for the system, and may include/communicate with any number of input and/or output hardware, such as a computer mouse, keyboard, entry pad, actuable display, networked or connected second computer, other GUI aspects, camera(s) or scanner(s), sensor(s), sensor/motor(s), range-finders, GPS systems, receivers(s), transmitter(s), transceiver(s), transceiving tag(s) (both active and passive, resonant or otherwise-uniquely-responding to an input signal with a uniquely-identifiable product signal), antennas, electromagnetic actuator (s), mixing board, reel-to-reel tape recorder, external hard disk recorder (solid state or rotary), additional hardware controls and actuators, light sources, speakers, additional video and/or sound editing system or gear, filters, computer display screen or touch screen. It is to be understood that the input and output of the system, and the tag(s), may be in any useable form, including, but not limited to, signals, data, commands/ instructions and output for presentation and manipulation by a user in a GUI. Such a GUI hardware unit and other input/ output devices could implement a user interface created by machine-readable means, such as software, permitting the user to carry out any of the user settings, commands and input/output discussed above, and elsewhere in this application.

701, 703, 705, and 707 are connected and able to communicate communications, transmissions and instructions via system busses 775. Storage media and/or hard disk recorder and/or cloud storage port or connection device 705 is capable of providing mass storage for the system, and may be a computer-readable medium, may be a connected mass storage device (e.g., flash drive or other drive connected to a U.S.B. port or Wi-Fi) may use back-end (with or without middle-ware) or cloud storage over a network (e.g., the internet) as either a memory backup for an internal mass storage device or as a primary memory storage means, or may simply be an internal mass storage device, such as a computer hard drive or optical drive.

Generally speaking, the system may be implemented as a client/server arrangement, where features of the invention are performed on a remote server, networked to the client and made a client and server by software on both the client computer and server computer. Input and output devices may deliver their input and receive output by any known means of communicating and/or transmitting communications, signals, commands and/or data input/output, including, but not limited to, input through the devices illustrated in examples shown as 717, such as 709, 711, 713, 715 and 777 and any other devices, hardware or other input/output generating and receiving aspects. Any phenomenon that may be sensed may be managed, manipulated and distributed and may be taken or converted as input or output through any sensor or carrier known in the art, or that may become so known. It is understood that any form of electromagnetism, compression wave or other sensory phenomenon may include such sensory directional and 3D locational information, which may also be made possible by multiple locations of sensing, preferably, in a similar, if not identical, time frame. The system may condition, select all or part of, alter and/or generate composites from all or part of such direct or analog image or other sensory transmissions, including physical samples (such as DNA, fingerprints, iris, and other biometric samples or scans) and may combine them with other forms of data, such as image files, dossiers or metadata, if such direct or data encoded sources are used.

While the illustrated system example 700 may be helpful to understand the implementation of aspects of the invention, it is understood that any form of computer system may be used to implement many control system and other aspects of the invention—for example, a simpler computer system containing just a processor (datapath and control) for executing instructions from a memory or transmission source. The aspects or features set forth may be implemented with, and in any combination of, digital electronic circuitry, hardware, software, firmware, or in analog or direct (such as electromagnetic wave-based, physical wave-based or analog electronic, magnetic or direct transmission, without translation and the attendant degradation, of the medium) systems or circuitry or associational storage and transmission, any of which may be aided with enhancing media from external hardware and software, optionally, by wired or wireless networked connection, such as by LAN, WAN or the many connections forming the internet or local networks. The system can be embodied in a tangibly-stored computer program, as by a machine-readable medium and propagated signal, for execution by a programmable processor. The method steps of the embodiments of the present invention also may be performed by such a programmable processor, executing a program of instructions, operating on input and output, and generating output. A computer program includes instructions for a computer to carry out a particular activity to bring about a particular result, and may be written in any programming language, including compiled and uncompiled, interpreted languages, assembly languages and machine language, and can be deployed in any form, including a complete program, module, component, subroutine, or other suitable routine for a computer program.

Figure 8:
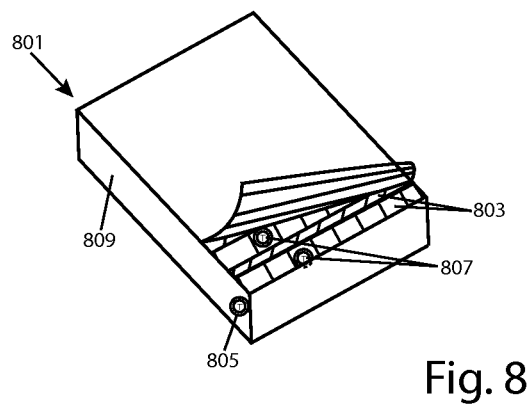
FIG. 8 is a perspective drawing of partially-opened food packaging containing several food bars, implementing a nutritional inventory and tracking system according to aspects of the present invention.

FIG. 8 is a perspective drawing of a partially-opened food packaging container 801, containing several food bars, such as the examples shown as 803. Together, and with further aspects described below, food bars 803 and their packaging 801 may implement a nutritional inventory and tracking system according to aspects of the present invention. That system may also comprise a computer hardware and software control system, examples of which are discussed in greater detail above, and, specifically, with reference to FIG. 7.

Container 801 may include, contain or comprise at least one master tag 805, which, as with other tags discussed above, may be locally powered or powered by an external aspect, such as the control system, and may be uniquely identifiable (containing, for example, UPC information, or other encoding readable by the system to determine product information to be tracked by the system). As with other tag aspects discussed above, to be readable and trackable by the control system, the master tag 805 may reflect, partially reflect, resonate, partially absorb or otherwise process and return a radiation or other signal sent from an aspect external to the master tag 105, such as an aspect of the control system, or inventory tags (which will be discussed below) and such efferent signals may be unique and uniquely originate from each tag in response to particular signals received. Alternatively, or in addition, the master tag itself may broadcast unique radiation and other signals, readable by the control system (for example, via an antenna aspect of the control system) and containing the same information as a signal processed and returned by the master tag 805.

Each food bar item 803 may be individually packaged, with packaging that contains additional, uniquely identifiable inventory tags 807. Alternatively, and as will discussed in greater detail below, bar items 803 may themselves contain consumable or removable inventory tags 807. As with other secondary tags, set forth above, inventory tags 807 may uniquely respond with an uniquely identifying signal (for example, by harmonic resonation, partial absorption, partial reflection, or a combination of any of these) to unique signals received by them from an external source, such as an aspect of the control system, master tag 805, or another external source, by emitting their own uniquely-identifiable signals. Also as with other tags set forth in this application, tags 807 may, alternatively, or in addition, themselves broadcast unique radiation and/or other signals, readable by the control system (for example, via an antenna aspect of the control system). In any event, in a preferred embodiment, a unique signal so emitted by inventory tags 807 may then interact with master tag 805, causing it to uniquely respond by emitting its own unique signal, which is unique to the both the source(s) signal and the master tag, and uniquely identifiable by the control system, for example, to determine the number of tags, and other meta data. Master tag 805 may be uniquely situated, bridging both sides (inside and outside) of the outer wall 809 of a food container, such that signals from the master tag are easier for an external control system to read. In addition, where a master tag simultaneously receives and responds to multiple uniquely identifiable symbols from differing numbers and identities of food items 803 within the container 801, it may produce a unique summation signal(s), which is readable by the system to determine a count and identity of all food items within the container, as well as the unique information discussed above concerning the container itself. In this way, the control system can rapidly determine the identity and amounts of available or consumed food items 803, within each unique container 801 that may, for example, be within a larger inventory managed and tracked by the control system. Master tag 805 also may be uniquely capable in other respects, for example, in receiving power from a control system and creating an efferent signal. Master tag 805 may also have the ability to perceptibly alter its signal that it returns to the base station in reaction to signals, which may be with the aid of such external power, based on far weaker received signals from other tags. The same capability differentials may exist for other tag sets (for example, for tracking personal activity) a main signal element, and other signal elements, within the context of a consumable tag, as discussed below.

Figure 9:
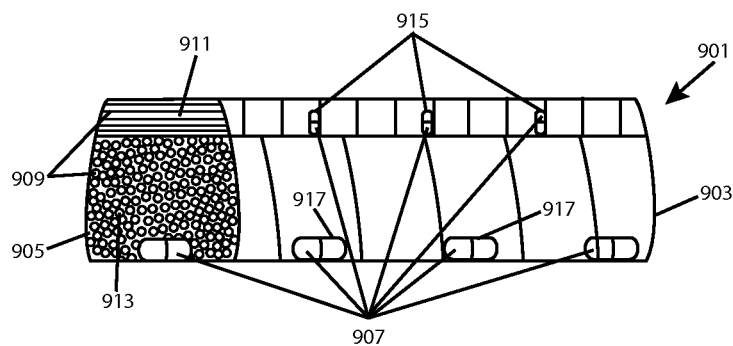
FIG. 9 is a perspective drawing of a partially-consumed individual food bar item, similar to the food bars discussed above, with reference to FIG. 8, and comprising multiple inventory tags and inventory tag types at spatial intervals throughout the item, which may be used in conjunction with a consumption tracking system according to aspects of the present invention, and in accordance with aspects of the present invention.

FIG. 9 is a perspective drawing of a partially-consumed individual food bar item 901, such as the food bars 803 discussed above, with reference to FIG. 8, and comprising multiple inventory tags 907 and inventory tag types at spatial intervals throughout the item, in accordance with aspects of the present invention. Food bar 901 comprises entirely relatively safely consumable material, including tags 907, and further comprises an edible outer layer or surface 903. Food bar 901 has, however, been bitten into by a consuming user, removing part of the bar 901, and, as a result, a left-hand side 905 of the bar is shown that is not covered by outer layer or surface 903. As a result, from side 905, one may see internal food stuff 909 of two varieties: an upper nougat 911 and a main vitamin and protein blend 913, in separate sections of the bar 901. Embedded in each food stuff 909 are individually uniquely identifiable consumable tags 907, and, in some embodiments, those tags may be uniquely identifiable based on which food stuff they are embedded in. In other words, tags 907 may be of two types, each with an at least partial encoding in signals transmitted from them reflecting the type of food stuff they are embedded in: nougat tags, such as those examples shown as 915, and blend tags, such as those examples shown as 917. In addition, in some embodiments, tags 907 may be differentiated in their efferent signal encoding based on their location within bar 901. The tags 907 are preferably placed at uniform distances from one another throughout the bar and each food stuff, or randomly so distributed, such that a count of such tags may correspond with a proportion of food remaining, in which they are deposited. In this way, a control system pinging or otherwise sending signals to the tags (which may be through a master tag(s), as discussed above), or simply receiving their efferent signals, can infer how much of the bar 901 as a whole, and how much of each food stuff has been consumed. As will be explained further, below, the identity of consumer users ingesting the food stuffs, and more complex data, such as food absorption and caloric uptake, can also be determined by more complex types of consumable tags. But, in some embodiments, each tag 907 may not be uniquely identifiable in comparison to all other tags 907, but, instead, they are identifiable as tags of a common type, and a control system may infer some (albeit less) consumption information from counts of instances of signals received when scanning a food unit, such as food bar 901. In one embodiment, the identity of a consumer user of the above proportional food consumption system may be made by the control system utilizing biometric data recognition. In another embodiment, the identity of a consumer user of the above proportional food consumption system may be made by tags or signal elements held and associated with the consumer. In this latter embodiment, the system may identify the consumer as consuming the tagged food by collocation of tags or signal elements embedded in consumed and unconsumed sections of food and/or agent-containing items.

Figure 10:
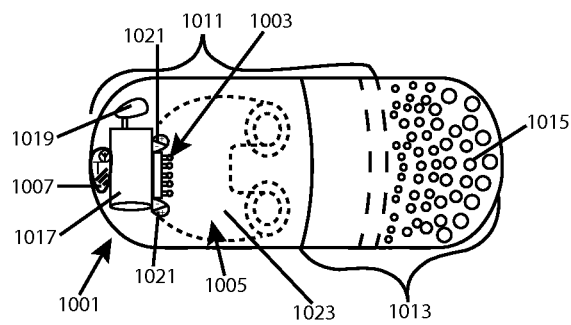
FIG. 10 depicts an exemplary consumable tag, such as the consumable tags discussed above, but also containing a sensor array and sensor-exposing pump/conduit, which may comprise an ion pump/conduit, which may be used in conjunction with a consumption tracking system according to aspects of the present invention, and in accordance with aspects of the present invention.

FIG. 10 depicts an exemplary consumable tag 1001, such as the consumable tags discussed above, but also containing a sensor array 1003 and sensor-exposing pump/conduit 1005, which may comprise an ion pump/conduit. Consumable tag 1001 is preferably streamlined for passage through a consumer/user's digestive tract, and, as mentioned above, composed of materials safe for human or other animal consumption. Tags such as example 1001 comprise an antenna or other radiative signal/response element 1007, which, as discussed in detail above, may emit a uniquely-identifying signal, from its own power source and/or an external power source, and may so emit unique signals in response to receiving pinging or other signals unique to a source (such as a control system). As discussed above, such unique signals may be unit (tag) specific in their identification properties, and may include useful information concerning the tag and/or associated items (such as food stuffs consumed with the tag), and/or may uniquely identify types of items associated with the type of tag. In addition, tag 1001 may comprise multiple functional sections such as: (1) a sensory/communications section 1011 and (2) a deployment/hatch section 1013, which preferably partially overlap to maintain an airtight seal prior to deployment (in consumption by ingestion). Those multiple sections may disengage upon some stimulus related to a point in digestion, or selectively disengage upon signaled instruction from a control system, but preferably disengage upon ingestion by enteric dissolution of one of the section's outer linings. Upon so disengaging, deployment/hatch section 1013 may, optionally, deploy a payload for consumption, such as a medicine or vitamin payload, 1015. In such event, the sensor array 1003 may test for medicinal, vitamin or other payload concentration and/or reaction products, but, if embedded and associated with food, sensor array 1003 may test for the concentration and/or reaction products of the associated food, or components thereof, to infer absorption and digestion information, as well as other gastrointestinal conditions and activities. When the sensor-comprising tag 1001 is deployed, and sections 1011 and 1015 are separated, sensor array 1003 is preferably then at least partially exposed within the pathway of the digestive fluid surrounding it after ingestion, which may be pumped across it with the aid of pump/conduit 1005. Pump/conduit 1005 may use ion-driving variable charge components, such as those shown as 1021, to polarize and drive, or simply drive ions in the surrounding fluid through a channel 1023 containing at least part of the sensor array 1003 with rhythmic, ion-moving charge oscillation patterns. For example, the lower component 1021 may take a positive charge in one instant, pulling oppositely charged ions toward it after the upper component 1021 has taken on the same charge, locking such ions from passing from above and, as a result, create an inward-rushing current from the lower section of channel 1023. The upper component 1021 may then release its positive charge and permit the flow to continue upward, while the lower component 1021 begins reversing its charge, as the ions pass beyond it, upward. But other, for example, electromechanical, pump methods may also, or alternatively, be used. A local processor, such as a CPU, 1017, may communicate with, run and manage sensor array 1003 and such a pump, with the aid of a power source 1019, but an at least partially external power source and/or processor may also, or alternatively, aid in running, managing and powering the sensor array 1003, for example, by emitting radiative power and signals, both powering and managing the array.

Figure 11:
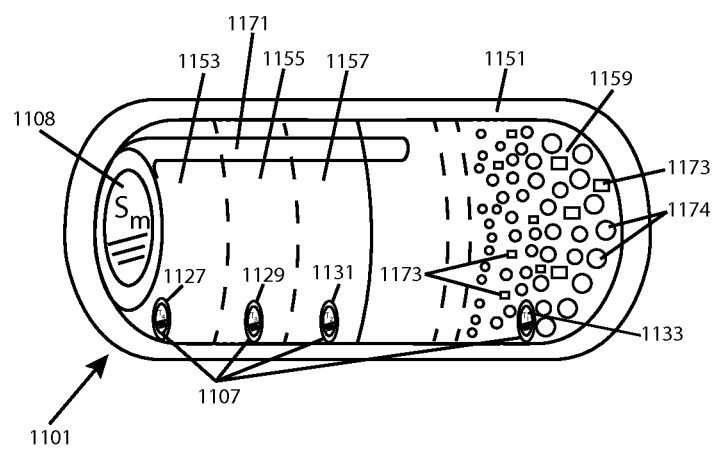
FIG. 11 depicts an exemplary consumable tag comprising multiple signal/response elements, which may interact with one another as well as a control system, in accordance with aspects of the present invention.

FIG. 11 depicts an exemplary consumable tag 1101 comprising multiple signal/response elements 1107, which may interact with one another as well as a control system, in accordance with aspects of the present invention. Each signal element 1107 is held within a separate section of tag 1101, such that, as each chamber may variably and separately open to the outer environment (i.e., a consumer user's digestive tract) at selectably different times and empty and deliver a payload (for example, of medicine, vitamins, markers and/or other agents) the signal element 1107 held in that section is removed from the tag 1101. By being removed from the tag 1101, any signal element may then no longer communicate with a main signal element 1108, which (owing to its positioning, size and/or different shielding from the exterior components of tag 1101 and signal communications properties) is more capable of communicating with a control system (e.g., sending and/or receiving signals from the control system's antenna) than the remainder of signal elements 1107. However, owing to their proximity and other properties relative to main signal element 1108, the remainder of the signal elements 1107 are able to communicate with and alter or condition signals emitted from the main signal element 1108, in such a way that main signal element 1108's signals to and from a control system will indicate the presence (and, in some embodiments) other properties of those remaining signal elements 1107. In one embodiment, signal elements such as 1107 may communicate exclusively with the main signal element 1108, rather than with other signal elements or direct communication with a control system. The usefulness of these properties will be better understood from the further discussion, below.

Tag 1101 may include an outer coating or shell layer 1151. Layer 1151 is preferably optimized to survive and ease passage through at least part of a user's upper digestive tract, such as the mouth and esophagus. After ingestion by a consumer user, shell layer 1151 may dissolve, to expose subcoatings and surrounding layers. For example, each payload compartment, including compartments 1153, 1155, 1157 and 1159, may comprise its own unique signal element 1107-1127, 1129, 1131 and 1133, respectively—and its own unique payload and coatings. Owing to the different properties of their different coatings, the compartments may variably dissolve and open, in any desired order, while maintaining an effective distance for signal transmission between any of their signal elements (if still held) and main signal element 1108, with the aid of a non-dissolving, or more slowly dissolving, compartment-linking bridge 1171, which is attached to and holds each compartment together with main signal element 1108, and holds the main signal element. A similar non-dissolving or more slowly dissolving material may be used to separate the chambers from one another, where they abut. In some embodiments, signals received by signal elements 1107 may trigger the selective energizing of system-selected signal element(s), to create a catalyzing effect for a reagent, either for selectively dissolving a compartment coating or for affecting a medicinal reaction (such as between reagent 1173 and reagent 1174 in compartment 1159), by creating reaction energy necessary for such chemical reactions, or actuating mechanisms dependent on such energy. In such embodiments, main signal element 1108 may serve as a conduit, intermediary or bridge to carry such reaction and other actuation activating signals and energy to individually-selected signal elements 1107. For example, if a physician or medical technician and/or control system chooses to precisely control the moment of deployment of a medicine within a patient's digestive tract (or blood stream, if tag 1101 is ingested) he/she/it may track the location of tag 1101 via main signal element 1108, and use main signal element 1108 to actuate individually-selected compartments for actuation at precisely selected points for deployment of medicine and other agents.

In some embodiments of the invention, inferential activity data, other than from sensor data or background and environmental (base station, beacon, or emanating from other personal activity areas than the user's) signal data, may aid in further defining a user's tracked activities and/or consumption data. For example, if a user provides access to his or her financial or other systematic data relating to food consumption, that data indicating consumption, location attendance, and other such data, that data may be applied as a factor by a computer hardware and software control system to an activity and/or consumption assessment, recording and an analysis program also incorporating or applying the other sensed and recorded data and signal types discussed in this application. In some embodiments, a specialized program, with accounts held by user's and participating venues, may be comprised within the system to aid in specialized information sharing to improve activity and consumption-related data. For example, if both a restaurant and restaurant patron participates in such a program, the patron's food consumption data (for example, from the restaurant billing system) may share enable the extraction of nutritional information, for use by the control system in recording and analyzing, and reporting on the patron's consumption-relevant data. Other personal activity, consumption and health data sensors of a wide variety may also supply such inferential data, or direct data, such as waste sensors placed in lavatories, and local environmental (e.g., air quality) sensors.

In some embodiments, a control system tracking a user's activities in accordance with aspects of the present invention may provide feedback, which may be live or real-time feedback, regarding the qualities of personal activity, which may be enriched by any of the sources of activity-relevant data discussed above. For example, proper speed and form, and/or deviations therefrom, for athletic movements may be assessed by the control system using a goal-form library of movement patterns for a matched activity, and relayed to a user or administrator (e.g., coach) on a GUI.

I claim:

1. A system for sensing, defining, recording, analyzing and controlling consumption and administration of food or other agents by a consumer user, comprising:
    (a) a master tag(s) within packaging for food or other agent-containing items, wherein the master tag(s) comprises hardware configured to communicate with a control system by receiving and transmitting signals;
    (b) computer hardware and software configured to transmit to said master tag(s) a signal with embedded information concerning the food or other agent-containing items and said packaging;
    (c) wherein said at least one of said master tag(s) is configured to communicate signals to and from other tag(s) and/or signal elements associated with individual food or other agent items, and to modify the course of said administration during said course of said consumption and administration.

2. The system for sensing, defining, recording, analyzing and controlling consumption and administration of food or other agents by a consumer user of claim 1, wherein at least one of said other tag(s) and/or signal elements is configured to responding to receiving an encoded signal with a signal uniquely identifying a particular food or other agent-containing item, wherein said uniquely identifying a particular food or other agent-containing item confirms:
    (a) the presence or absence of the particular food or other agent-containing item; and
    (b) a comprised food or other agent type within said particular food or other agent-containing item;
    wherein confirmation of said presence or absence of the particular food or other agent-containing item and said comprised food or other agent type condition(s) efferent signal properties of the master tag in subsequent communication with a control system.

3. The system for sensing, defining, recording, analyzing and controlling consumption and administration of food or other agents by a consumer user of claim 2, wherein the system comprises:
    at least one enhanced item of food and/or agent(s) containing a plurality of tags and/or signal elements embedded periodically throughout said at least one enhanced food and/or agent(s) such that, when said at least one enhanced item of food and/or agent(s) are partially consumed, any remaining tag and/or signal element in an un-consumed section of said at least one enhanced item of food and/or agent(s) is configured to be used by a control system to infer the amount and/or percentage of said enhanced item of food and/or agent(s) consumed.

4. The system for sensing, defining, recording, analyzing and controlling consumption and administration of food or other agents by a consumer user of claim 3, wherein a control system is configured to determine or infer the identity of a consumer user consuming said at least one enhanced item food and/or agent(s), or parts thereof, with tag(s) and/or signal elements on or about the consumer/user, and the collocation of said tag(s) and/or signal elements on or about the consumer/user with the tag(s) and/or signal elements in consumed and unconsumed sections of food and/or agent(s)-containing items.

5. The system for sensing, defining, recording, analyzing and controlling consumption and administration of food or other agents by a consumer user of claim 2, wherein said other tag(s) and/or signal elements are of specific types associated with and uniquely identifying types of food and/or agent with which they are associated.

6. The system for sensing, defining, recording, analyzing and controlling consumption and administration of food or other agents by a consumer user of claim 5, wherein said other tag(s) and/or signal elements of specific types are associated with and configured to uniquely identify types of food and/or agent within a single food and/or other agent item.

7. The system for sensing, defining, recording, analyzing and controlling consumption and administration of food or other agents by a consumer of claim 1, comprising:
    (e) analytical and food- or other agent-releasing hardware within a consumable device,
    (f) wherein said consumable device comprises said other tag(s) and/or signal elements associated with individual food or other agent items.

8. The system for sensing, defining, recording, analyzing and controlling consumption and administration of food or other agents by a consumer of claim 7, wherein:
    (g) said analytical and releasing hardware within said consumable device:
        (i) controls the administration of said food or other agents in an administration event;
        (ii) based on blood or other bodily fluid analytics carried out by said device while immersed in said blood or other bodily fluid during said administration event.

9. A system for sensing, defining, recording, analyzing and controlling consumption and administration of food or other agents by a consumer, comprising:
    (a) computer hardware and software for transmitting and receiving a uniquely identifiable signal to and from a consumable tag;
    (b) a consumable tag comprising a main signal element configured to:
        (i) communicate with a control system;
        (ii) communicate with other signal elements;
        (iii) monitor chemical reaction products in the blood stream or another bodily fluid; and
        (iv) alter the dosage or other administration of said food or other agents based on monitoring said chemical reaction products;
    wherein said other signal elements are configured to communicate exclusively with the main signal element.

10. The system for sensing, defining, recording, analyzing and controlling consumption and administration of food or other agents by a consumer of claim 9, wherein said other signal elements are configured to respond to signals from the main signal element with uniquely-identifiable signals which alter or otherwise condition signals from the main signal element to the control system; and the control system is configured to be modified in its transmission capabilities by said uniquely-identifiable signals from said other signal elements.

11. The system for sensing, defining, recording, analyzing and controlling consumption and administration of food or other agents by a consumer of claim 10, wherein a control system is configured to infer the presence of individual signal elements within said consumable tag.

12. The system for sensing, defining, recording, analyzing and controlling consumption and administration of food or other agents by a consumer of claim 11, wherein said individual signal elements are placed in separated chambers with separate payloads wherein said chambers and payloads are configured to be deployed separately.

13. The system for sensing, defining, recording, analyzing and controlling consumption and administration of food or other agents by a consumer of claim 12, wherein a control system is configured to infer at least one status of deployment of food or other agent(s) in a consumer user.

14. The system for sensing, defining, recording, analyzing and controlling consumption and administration of food or other agents by a consumer of claim 12, wherein a control system is configured to individually and selectively actuate the deployment of said food and/or agent(s) from said chambers, in any order and at a time of the control system or a user's choosing.

15. The system for sensing, defining, recording, analyzing and controlling consumption and administration of food or other agents by a consumer of claim 14, wherein a control system is configured to individually and selectively control reaction energy or other catalysis of chemical reactions of, or create mechanical actuation within, said chambers.

16. A system for sensing, defining, recording, analyzing and controlling consumption and administration of food or other agents by a consumer, comprising:
    a consumable tag;
    a signal/response element;
    a sensor array, pump and fluid conduit configured to sense, if immersed therein, the presence of food or another agent in a consumer user's digestive tract or bloodstream;
    computer hardware and software for configured to transmit and receive a uniquely identifiable signal to and from said consumable tag;
    wherein said consumable tag comprises said signal/response element
    and wherein said signal/response element is configured to selectively drive actuation of said sensor array, pump and fluid conduit, which control the administration of said food or other agents in real-time.

17. The system for sensing, defining, recording, analyzing and controlling consumption and administration of food or other agents by a consumer of claim 16, wherein said pump comprises an ion drive pump.

18. The system for sensing, defining, recording, analyzing and controlling consumption and administration of food or other agents by a consumer of claim 16, wherein said consumable tag comprises at least two sections.

19. The system for sensing, defining, recording, analyzing and controlling consumption and administration of food or other agents by a consumer of claim 18, wherein said two sections comprise a payload section and a sensory section.

20. The system for sensing, defining, recording, analyzing and controlling consumption and administration of food or other agents by a consumer of claim 16, wherein said pump and/or said sensor array are externally powered.

* * * * *